United States Patent [19]

Komissarova et al.

[11] Patent Number: 5,731,349
[45] Date of Patent: Mar. 24, 1998

[54] MEDICINAL PREPARATION OF ANTISTRESS, STESS-PROTECTIVE AND NOOTROPIC EFFECT

[76] Inventors: Irina Alexeevna Komissarova, ulitsa Medikov, 24, kv.47.; Julia Vasileivna Gudkova, ulitsa Barzarina, 9, kv.94; Tatyana Dmitrievna Soldatenkova, Pokrovsky bulvar, 14/5, kv.73; Tatyana Tikhonovna Kondrashova, ulitsa Severodvinskaya, 9, kv.305; Natalya Mikhailovna Burbenskaya, Moskovskaya oblast, Ozersky raion, selo Sennitsy, all of Moscow, Russian Federation

[21] Appl. No.: 701,147

[22] Filed: Aug. 21, 1996

Related U.S. Application Data

[62] Division of Ser. No. 119,050, filed as PCT/RU92/00005 Jan. 10, 1992, Pat. No. 5,643,954.

[51] Int. Cl.$^6$ ................................ A61K 31/195
[52] U.S. Cl. ................ 514/561; 514/546; 514/643; 514/646
[58] Field of Search ................ 514/546, 561, 514/643, 646

[56] References Cited

U.S. PATENT DOCUMENTS 4,438,144  3/1984  Blackburn ................ 514/561
4,562,205  12/1985  Cavalier ................ 514/546
4,871,550  10/1989  Millman ................ 514/561

FOREIGN PATENT DOCUMENTS 243783  4/1980  France .

OTHER PUBLICATIONS

The Merck Index, 10th Ed (1983) Abstract No. 5917.

Refcrativny Zhurnal "Khimia" vol. A No. 22, Viniti, 1991, p. 60, Abstract No. 22, 0214P.

Abstracts Jounal, 19, Chemistry, 190 Technology of Organic Medicinal Agents, Veterinary Agents Pesticides, Moscow, 1991, Entries 220211 to 220219.

Technology of Drugs, 1980, vol. 1 pp. 281, 335.

*Primary Examiner*—Kevin Weddington
*Attorney, Agent, or Firm*—Ladas & Parry

[57] ABSTRACT

A pharmaceutical preparation of antistress, stress-protective and nootropic effect contains an effective substance represented by an amino-acid glycine or its pharmaceutically acceptable salt.

A method of prophylaxis and curing of stress states and also increasing mental workability consists in sublingually administering an effective amount of the preparation of patent protection sought.

4 Claims, No Drawings

MEDICINAL PREPARATION OF ANTISTRESS, STESS-PROTECTIVE AND NOOTROPIC EFFECT

This is a divisional of application Ser. No. 08/119,050 filed on Sep. 10, 1993 now U.S. Pat. No. 5,643,954, and International Application PCT/RU92/00005 filed on Jan. 10, 1992 and which designated the U.S.

FIELD OF TECHNOLOGY

The present invention relates to medicine, more specifically, to a new medicinal preparation of antistress, stress-protective and nootropic effect.

PRIOR ART

The most frequent reaction of a person in a stress situation is psycho-emotional strain accompanied by excitement, anxiety, the worsening of memory and attention and is manifested in irrational and inadequate forms of behavior, in the decline and disorders of mental capacity, speed of reaction, in the increased number of erroneous decisions etc. Similar disorders are observed in various diseases (neuroses, neurosis-like states, astheno-neurofic reactions, to mention just few), and what is more, the degree of these disorders is increased in the case of acute and chronic stress influences.

In this connection, of substantial importance is a search for and preparation of drugs abating and preventing the effect of a stress factor and also displaying nootropic properties (increasing attention, improving memory and mental capacity and also stability of the brain aggressive influences).

Inasmuch as psycho-emotional strain is the response of a human body to various excessive stimuli, then for purposes of eliminating this strain, use is made of calming drugs with tranquilizers of the benzctiasepine series being widely known and most frequently used, as well as the derivatives of gammaaminobutyric acid (GABA)-pherdbute, baclophene, lyoresal which at the same time exhibit a nootropic effect (D. MashkovSky. "Medicinal drugs", Moscow, MEDITSINA Publishers, 1988; part I, pp. 70–79, 122–123). However, the above identified tranquilizers and derivatives (GABA) possess serious side-effects. Their doses are accompanied by drowsiness, depression, dizziness, lowered psychomotor reactions, an awkward gait, menstrual cycle disorders, libido and is contraindicated for persons whose behavior requires rapid and exact psychic and motor reactions. Besides this, prolonged use of tranquilizers affects mental working capacity and forms toxicomania.

A number of GABA derivatives are widely known and applied as nootropic drugs; however, they do not posses the antistressor or stress-protective effect (Mashkovsky. "Medicinal drugs", 1983, MEDITSINA Publishers, part I, pp. 117, 123).

It is known to use glycine as an ingredient of the preparation Mega 3 Vitamins/Minerals, by the firm Ortho-Biotics, which is used in stress states and also for enhancing intellectual working capacity (Professional Ortho-Biotics, Catalogue, 1989, CH, 1203 Geneva, Pharmacie Des Charmilles, p. 18). Alongside with said glycine, however, this preparation incorporates over 34 different ingredients, including vitamins, displaying an allergizing effect and has a high price. Moreover, it contains a tryptophan whose application in pharmaeeutieais and food additions has currently been prohibited by EDA (December of 1989).

DISCLOSURE OF THE INVENTION

The claimed preparation is a new one and has not yet been described in the literature. It is the principal object of the invention to develop a new medicinal drag possessing antistress, stress-protective and nootropie effects and also high activity; more than that, it is non-toxic and produces no side-effects.

The task has been solved owing to the fact that the claimed preparation comprising an active substance and a pharmaceutical cartier contains, according to the invention, the active substance represented by an amino-acid-glycine (glycocol, aminoacetic acid) of the following formula:

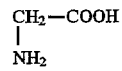

The preparation under examination demonstrates highly effective antistress, stress-protective and hoottopic effects and finds a variety of applications in the prophylaxis and treatment of neuroses and neurosis-like states, the residual phenomena of craniocerebral injuries and neuroinfections, astheno-vegetative disorders, in case of chronic alcohol intoxication and alcoholic abstinence and also for enhancing mental capacity.

The medicinal preparation can be used in the form of a powder, a saturated solution or tablets. Preferably it is applied sublingually in the form of tablets containing active substance in an amount of from 0.1 to 0.2 g per tablet. Preferably, the medicinal contains methylcellulose as a pharmaceutical vehicle in an amount of from 0.5 to 2 wt. %. The active substance of the claimed preparation is obtained by a chemical synthesis, biotechnologically or from animal tissues.

PREFERRED EMBODIMENT OF THE INVENTION

The active ingredient of the claimed preparation is an aliphatic amino-acid glycocol. Said amino-acid is a natural compound contained in animal tissues and is substantially a powdery substance of white color and without smell; it is readily soluble in water and alkaline solutions, but poorly soluble in ethyl alcohols and ethers.

The claimed preparation has been examined in experiments on animals and in clinics on patients (humans).

The antistress, stress-protective and neurotropic effects of the claimed preparation were studied in mature male rats weighing from 200 to 300 g and on immature male rats weighing from 30 to 40 g and/or 60 to 80 g and also ontoice weighing from 18 to 29 g.

The study of influence of the claimed preparation on the behavior of animals in an "open field" test after an acute stress action was performed on 20-day-old young male rats weighing 30–40 g. The test and control young rats were subjected to a single electric painful influence in a matter of a second ("electric floor" 59 hertz, 35 v). Prior to influence (before 20 min) a water-dissolved preparation had been administered into the tested young rats on their tongue root in a dose of 2 mg/kg of the mass; a control group was given a corresponding mount of water. Sixty minutes after, the behavior of the animals was investigated in the "open field" test. Additionally use was made, by way of control, of the results of evaluation of the behavior of the above-mentioned 20-day-old young rats in the "open field" test, which received only water 60 minutes before testing. (cf. Table I).

TABLE 1

| Animal Groups | Behavior parameters, $M \pm m$ | | | | | |
|---|---|---|---|---|---|---|
| | 1 | 2 | 3 | 4 | 5 | 6 |
| Test (electric painful influence + claimed preparation) | 4.50** ± 13.46 | 1.0** ± 0.28 | 0 | 1.0** ± 0.01 | 0.4 ± 0.28 | 0.4** ± 0.42 |
| I Control (electric painful influence without the claimed preparation) | 101.0* ± 9.68 | 3.3 ± 0.48 | 0 | 11.0 ± 2.74 | 1.2 ± 0.32 | 2.0 ± 0.48 |
| II Control (without electric painful influence and with no claimed preparation) | 28.0 ± 12.98 | — | — | 1.7 ± 0.34 | 1.0 ± 0.34 | 1.0 ± 1.03 |

Note:
1. Number of movements; 2. Removed from a floor's edge; 3. Intersection of a floor's center; 4. Standing postures; 5. Defecation; 6. Washes.
*a difference with II Control is proved, $p < 0.05$;
**a difference with I Control is proved, $p < 0.05$.

As seen from Table 1, the claimed preparation as preliminarily administered displays a stress-protective effect and considerably reduces on-stress-dependent excitement manifestations as to both motor factors and emotional-cognitive activity.

There has been studied a stress-protective action of the claimed preparation in an "electric floor" test, in which after a single electric painful irritation (stimulation), reaction components—emotional (squeak), motor (jumps) and aggressive (fights) were registered for a pair of male mice. The claimed preparation administered 60 minutes before the experiment did not exert influence on an emotional reaction, somewhat (1–1.5 points) strengthened a motor component, but reduced the number of rights and increased an aggression reaction threshold by 5±0.8 v. The antistress and stress-protec. tive action of the claimed preparation has been studied on young rats weighing 30–40 g and grown-up male rats weighing 200–250 g with the use of a model of chronic electde painful influence. In test and control groups, for the purpose of assessing the effect the claimed preparation produces in testing operations, use was made of a test of consumption of 15% ethanol in the conditions of free choice between the ethanol and water, because the chronic stress influence is accompanied by an increased alcohol motivation and an increase in the consumed ethanol, for which purpose utilized was an "electric floor" (50 hertz, 30–40 v) in the case of the young rats and 60 v for the grown-up animals. In the test and control groups of animals, a determination was given during 7 days to an individual daily-consumption of 15% ethanol in the conditions of free choice between said 15% ethanol and water. Thereafter the young rats were subjected to q.aintuple electric painful influence, daily for 2 weeks, on the paws for 5 minutes, duration 1 sec.; the grown-up animals—tenfold influence for 10 minutes, duration 1 sec. Twenty minutes before painful irritation, the test group received the aqueous solution of the claimed preparation on the tongue root in a dose of from 1 to 2 mg/kg of the mass. The consol group received a corresponding volume of water. Over 3 weeks, consideration was given, in the conditions of free choice between the 15% ethanol and water, to the individual daily consumption of the 15% ethanol by the rats: 2 weeks during the time period of chronic stress influence and administration of the claimed preparation and 1 week after termination of said electric painful irritation (stimulation) and cancellation of the claimed preparation. The results are given in Table 2.

TABLE 2

Influence of the claimed preparation in case of chronic stress effect produced on the daily 15% ethanol consumption by rats
(in ml, $M \pm m$)

| Animal groups | Stages of Investigation | | | |
|---|---|---|---|---|
| | 1st Week | 2nd Week | 3rd Week | 4th Week |
| Young rats: | | | | |
| Test | 2.7 ± 0.2 | 4.4 ± 0.3 | 2.0 ± 0.2 | 1.6 ± 0.18 |
| Control | 2.5 ± 0.2 | 8.0 ± 0.4 | 6.7 ± 0.3 | 3.3 ± 0.3 |
| Confidence, p | — | <0.05 | <0.05 | <0.05 |
| Adult animals: | | | | |
| Test | 1.8 ± 0.08 | 3.4 ± 0.13 | 2.5 ± 0.15 | 2.3 ± 0.3 |
| Control | 1.9 ± 0.09 | 7.1 ± 0.96 | 8.4 ± 0.39 | 5.9 ± 0.2 |
| Confidence, p | — | <0.05 | <0.05 | <0.05 |

The data of Table 2 show that the claimed preparation diminishes the alcohol motivation of the animals, and along with this, its antistress effect does not depend on their age and is observed upon termination of its administration and electric painful stimulation. The antistress effect of the claimed preparation was also detected on the animals behavior. For instance, in the test rats' groups during the entire experiment a considerable reduction of aggressiveness and excitability vis-a-vis the control groups was seen.

It is commonly known that manipulations with animals (cell sapling, administration of substances, water included) are a unique stress factor and cause a prolonged state of excitement, disturbance, aggressiveness. To clear up the dependence of the anti stress effect of the claimed preparation on the nature of stress influence there was investigated the effect of the claimed preparation on 20-day-old rats with said preparation administered on the tongue root in a dose of 1 mg/kg of mass (test) and a corresponding amount of water (control) in the conditions of free choice between 15% ethanol and water. The results are given in Table 3.

TABLE 3

Influence of the claimed preparation on 15% ethanol daily consumed by rats in case of chronic emotional stress (in ml, M ± m)

| Animal groups | Stages of Examination | | | |
|---|---|---|---|---|
| | 1 Week | 2 Week | 3 Week | 4 Week |
| Test | 3.6 ± 0.3 | 4.0 ± 0.3 | 2.3 ± 0.3 | 2.7 ± 0.2 |
| Control | 3.6 ± 0.3 | 3.6 ± 0.3 | 6.7 ± 0.3 | 5.0 ± 0.3 |
| Confidence, p | — | <0.05 | <0.05 | <0.05 |

The data of Table 3 show that daily manipulations with the animus intensify alcohol motivation, and administration of the claimed preparation considerably reduces it. Thus, the antistress effect of the claimed preparation does not depend on the nature of the stress factor.

To detect the nootropic effect of the claimed preparation and find out the mechanisms of its action the effect produced by the preparation per se on neuro-physiological processes has been studied. Experiments were conducted in vivo on male mice weighing 18–22 g and male rats weighing 200–250 g, as well as in vitro on isolated organs: a guinea pig's ileum and a rat's seminal effervesces. A comparative examination was given to the influence of the claimed preparation and GABA derivative-phenibut on the orientation motive activity of mice with the automated registration of their movements, and what is more, the claimed preparation and phenibut were introduced intraperitoneally in the form of aqueous solutions, while the control group of animals were administered with a corresponding volume of water. The results are presented in Table 4.

TABLE 4

| Dose, mg/kg, weight | Tract | Number of animal a group | Number of movements in 10 min in register (M ± m) | | test confidence, p |
|---|---|---|---|---|---|
| | | | claimed prep. | phenibut | |
| Control | Intraperitoneally | 20 | 657 ± 96 | 269 ± 8.4 | <0.05 |
| 2 | " | 10 | 371 ± 56 | | <0.05 |
| 20 | " | 10 | 365 ± 79 | | <0.05 |
| 40 | " | 10 | 324 ± 56 | | <0.05 |
| 40 | Into stomach | 10 | 439 ± 70 | | <0.05 |
| 80 | Intraperitoneally | 10 | 398 ± 48 | | <0.05 |
| 100 | " | 10 | | 434 ± 4.4 | <0.01 |
| 200 | " | 10 | 275 ± 23 | 186 ± 8.7 | <0.01 |
| 500 | " | 10 | | 19 ± 3.0 | <0.01 |

As can really be seen from the table, administration of the claimed preparation 20 minutes before registration is accompanied by a reduction of animals' motor activity, but the degree of a decrease in orientation motive reactions does not depend on a dosage of the preparation claimed. Moreover, as regards the nature of a responsive reaction, the effect of the claimed preparation differs from that of phenibut.

Investigations were conducted to study an effect the claimed preparation has on the rectal temperature of mice. Introduction of the claimed preparation in a dose of 2.20, 40, 80 and 200 mg/kg of the weight of animals did not affect the temperature of the body, as distinct from tranquilizers under whose influence the temperature of the animal body is lowered. In order to grasp an idea of action of the claimed preparation a study was made of same in interaction test with hexenal effects in a dose of 60 mg/kg of the animal's weight, apomorphine in a dose of 2 mg/kg of the animal's weight, phenamine in a dose of 6 mg/kg, arecoline in dose of 25 mg/kg of the animal's weight with evaluation given to duration of latent periods of origination of hexenal/apomorphine/phenamine effects and duration of hexenal sleep, phenamine and apomorphine stereotypy and arecoline hyperkinesia. The results are given in Table 5. As seen from the table, pre-administration of the claimed preparation in a dose of from about 20 to about 60 mg/kg of the animal's weight tells on only increasing a latent period of said apomorphine and phenamine stereotypy. Duration of hexenal sleep and also duration and expression of phenamine and apomorphine stereotypy and arecoline hyperkinesia do not change.

Examination was also performed to find out an effect the claimed preparation produces on mice in testings with Corazol in a dose of 150 mg/kg of weight whose introduction in said dose causes the death of 100% of the animals after 2–4 minutes. The results are presented in Table 5 from which it follows that intragastric introduction of the claimed preparation 20 minutes before administration of Corazol is accompanied by an increased latent period of Corazol convulsions and some depression of the tonico-extensor component of a twitch paroxysm, but observable effects depend on a dosage of the claimed preparation anyway.

TABLE 5

Influence of claimed preparation in interaction tests on hexenal/phenamine/apomorphine/arecoline/Corazol effects in mice

| Dose, mg/kg of animal weight | Number of animals in a group | Effect characteristics, M ± m hexenal | |
|---|---|---|---|
| | | latent period, in min. | duration of sleep, in min. |
| Control Claimed preparation: | 10 | 36.0 ± 0.9 | 33.0 ± 2.5 |
| 2 | 10 | 4.5 ± 0.3 | 36.0 ± 1.8 |
| 40 | 8 | 4.5 ± 0.6 | 32.0 ± 1.9 |

TABLE 5-continued

Influence of claimed preparation in interaction tests on hexenal/phenamine/apomorphine/arecoline/Corazol effects in mice

| 200 | 8 | 3.8 ± 0.7 | 38.0 ± 1.9 |
|---|---|---|---| phenamine

| latent period, in sec | duration of stereotype, in min. |
|---|---|
| 98.0 ± 8.0 | 69.0 ± 3.2 |
| 110.0 ± 2.6 | 65.0 ± 2.5 |
| 115.0 ± 1.5 | 62.0 ± 1.6 |
| 120.0 ± 2.8* | 62.0 ± 2.1 | apomorphine

| latent period, in sec | duration of stereotype, in min. |
|---|---|
| 86.0 ± 3.0 | 21.0 ± 1.2 |
| 98.0 ± 1.5* | 20.0 ± 0.9 |
| 104.0 ± 0.9 | 22.0 ± 0.6 |
| 95.5 ± 0.8 | 20.0 ± 0.5 |

| Dose of claimed preparation, mg/kg of animal weight | Number of animals in a group | Effect of characteristic M ± m Arecoline | |
|---|---|---|---|
| | | hyperkinesia, duration, min | latent period, sec, |
| Control | 10 | 15.0 ± 0.9 | 34.0 ± 0.9 |
| Claimed preparation: | | | |
| 2 | 10 | 16.5 ± 0.4 | 39.0 ± 0.6* |
| 20 | 10 | 14.8 ± 1.2 | 41.0 ± 0.3* |
| 40 | 10 | 13.8 ± 0.9 | 49.0 ± 0.7* |
| 80 | 10 | 14.5 ± 0.9 | 45.0 ± 0.9* |
| 200 | 10 | 15.6 ± 0.8 | 42.5 ± 0.7* |

Corazol

| tonico-ex-tensor phase, min. | life-time, min. |
|---|---|
| 100 | 2.7 ± 0.5 |
| 100 | 2.5 ± 0.7 |
| 80 | 2.8 ± 0.8 |
| 70 | 2.4 ± 0.7 |
| 70 | 3.1 ± 0.9 |
| 70 | 2.4 ± 0.5 |

Note:
*difference with the control is actual, $p < 0.05$.

There has been conducted a comparative investigation of the claimed preparation and phenibut on rats in testing interaction with hexenal and Corazol. The results are given in Table 6.

TABLE 6

| | Hexenal Sleep duration, in min, M ± m | |
|---|---|---|
| Doses, mg/kg, weight | Claimed prepar. | Phenibut |
| Control | 33.0 ± 2.6 | 40.7 ± 4.1 |
| 2 | 36.0 ± 1.8 | — |
| 40 | 32.0 ± 1.9 | — |
| 100 | — | 110.0 ± 8.3 |
| 200 | 28.0 ± 1.9 | 130.0 ± 8.5 |
| Confidence, p | >0.1 | <0.05 |

TABLE 6-continued

| | Corazol Twitches, latent period, min., M ± m | |
|---|---|---|
| | Claimed preparation | Phenibut |
| Control | 34.0 ± 0.9 | 52.0 ± 3.9 |
| 20 | 41.0 ± 0.3 | — |
| 80 | 45.0 ± 0.9 | — |
| 100 | — | 53.0 ± 5.4 |
| 200 | 42.5 ± 0.7 | 50.0 ± 2.8 |
| Test confidence, p | <0.05 | — |

It follows from the table that the effects of the claimed preparation differ in principle from those of pherdbut whose effect is similar to the tranquilizers of a benzdiazepin series.

In view of the fact that Corazol interaction tests have revealed a weak antiparoxysmal action of the claimed preparation, its possible antiparoxysmal activity has been studied on mice in testing with Corazol/strychnine intravenous titration and electrical shock influence on models enabling one to specify the mechanism of suppressing the tonico-extensor component of twitch paroxysm. The results are given in Table 7, wherefrom it follows that the claimed preparation does not practically influence said strychnine effects and is inactive towards electrical-shock-caused paroxysms, though somewhat increasing a Corazol threshold dosage causing the outbreak of paroxysm and especially a tonico-extensor phase and death of the animals. Such data go to show the selective antagonism of the claimed preparation with respect to Corazol, rather than a direct antiparoxysmal effect thereof.

To specify the mechanism of action of the claimed preparation, its activity has been studied in tests on isolated smooth muscle objects (a rat's seminal effervesces and a guinea pig's ileum). By using a movable electrode tube and its sensors there was recorded the contracting activity of said objects in the presence of the claimed preparation, acetylcholine and adrenaline. The results are given in Table 8.

TABLE 8

| Claimed preparation, control concentration, $M \pm m$ | Amplitude of concentration, mm ($M \pm m$) and in % to Agonists | | | |
|---|---|---|---|---|
| | adrenaline (rat's seminal effervsece) | | acetylcholine (guinea pig's ileum) | |
| 1 | 2 | 3 | 4 | 5 |
| Control | $69.0 \pm 2.0$ | 100% | $107.0 \pm 2.5$ | 100% |
| Claimed preparation: | | | | |
| $1.10^{-6}$ | $65.0 \pm 1.29$ | 94% | $116.0 \pm 2.4$ | 109% |
| $1.10^{-5}$ | $57.0 \pm 0.8^*$ | 83% | $105.0 \pm 1.8$ | 99% |
| $1.10^{-4}$ | $45.0 \pm 0.6^*$ | 65.5% | $97.0 \pm 1.5$ | 89% |

*difference with the control is actual, $p < 0.05$.

The table data show that the claimed preparation suppresses the contracting responses to said seminal effervesce

TABLE 7

| Dose, mg/kg, of animal weight | Threshold doses Corazol 1% solution, ml, $M \pm m$ | |
|---|---|---|
| | Start of twitch | death of animal |
| 1 | 2 | 3 |
| Control | $0.084 \pm 0.008$ | $0.116 \pm 0.020$ |
| Claimed preparation (single administration): | | |
| 2 | $0.095 \pm 0.004$ | $0.119 \pm 0.006$ |
| 40 | $0.091 \pm 0.005$ | $0.130 \pm 0.006$ |
| 80 | $0.095 \pm 0.004$ | $0.135 \pm 0.007^*$ |
| 200 | $0.096 \pm 0.007$ | $0.130 \pm 0.08$ |
| Control | $0.092 \pm 0.005$ | $0.118 \pm 0.006$ |
| Claimed preparation (a week-long introduction): | | |
| 2 | $0.090 \pm 0.007$ | $0.119 \pm 0.004$ |
| 40 | $0.095 \pm 0.005$ | $0.163 \pm 0.005^*$ |

| Dose, mg/kg, of animal weight | Threshold doses Strychnine 0.01% solution, ml, $M \pm m$ | | Maximal electric shock | |
|---|---|---|---|---|
| | start of twitch | death of animal | tonico-extensor phase, % | death of animal, % |
| 1 | 4 | 5 | 6 | 7 |
| Control | $0.16 \pm 0.020$ | $0.19 \pm 0.030$ | 100 | 60 |
| Claimed preparation (single administration): | | | | |
| 2 | $0.17 \pm 0.008$ | $0.21 \pm 0.007$ | 100 | 70 |
| 40 | $0.18 \pm 0.007$ | $0.21 \pm 0.005$ | 100 | 40 |
| 80 | $0.17 \pm 0.005$ | $0.18 \pm 0.006$ | 100 | 40 |
| 200 | $0.15 \pm 0.008$ | $0.19 \pm 0.006$ | 100 | 70 |
| Control | | | 100 | 50 |
| Claimed preparation (a week-long introduction) | | | | |
| 2 | | | 100 | 60 |
| 40 | | | 100 | 40 |

*difference with the control is actual, $p < 0.05$.

adrenaline, without discovering antagonism with said acetylcholine. A weak and mild adrenoblocking action of the claimed preparation at a concentration of $1.10^{-5}$ and $1.10^{-4}$M testifies to its capability of interacting with adrenorgic receptors, particularly, with $alpha_1$ adrenoreceptors. By analogy with other known pharmacological preparations one can assume that the same interaction with said $alpha_1$-adrenoreceptors is manifested by the claimed preparation with brain adrenoreceptors, too, a factor that explains its antistressor activity in case of acute and chronic stress influence accompanied by an increase of said adrenaline in tissues.

There has been studied the influence of the claimed preparation on spontaneous bioelectrical activity of the brain of rats with its being recorded with animals with permanently implanted electrodes in free behavior. The Table 9 data show that with the dosage of 40 mg/kg of the animal weight, the claimed preparation, intraperitoneally introduced, tends to call for a synchronizing effect on an encephalogram, which came through an increased amplitude and electroencephalogram slow rhythm indices. However, this action of the claimed preparation differs from that of conventional preparations exerting synchronizing effect and influencing the amplitude and said slow rhythm index in the presence of the effect in the form of repeated episodes with a frequency of 1 to 2 times per hour during a 4- hour long experiment.

claimed preparation over 60 days in a dose of about 200 mg/kg of animal weight did not discover morphological and pathological changes thereof.

A study was made of the influence of the claimed preparation on mental capacity, its antistressor and stress-protective action on 20 healthy persons, 33 alcoholics and 154 children and teenagers of school age. The control groups of adults, children and teenagers received a placebo or did not receive the claimed preparation, the latter being taken once in a dose of 2mg/kg of weight sublingually or during a course of treatment over 14–30 days in a dose of 2 mg/kg twice-thrice a day. The examination of the effect producedby the claimed preparation was carried out through special tests (Tables of Krepelin, Schulte et at) enabling one to evaluate the rate of counting-calculating operations, attention short-lived memory, central nervous system state, the state of sensomotor reactions and the cardiovascular system.

To assess the influence the claimed preparation exerts on the speed of counting-computing operations, use was made

TABLE 9

Influence of the claimed preparation on bioelectric activity of rats' brain

| Preparation 1 | Dose, mg/kg animal weight 2 | Index. %, $M \pm m$ | | Amplitude, mV, $M \pm m$ | |
|---|---|---|---|---|---|
| | | slow activ. 3 | fast active. 4 | slow activ. 5 | fast activ. 6 |
| Control | | $12 \pm 1.9$ | $22 \pm 2.8$ | $277 \pm 10$ | $273 \pm 76$ |
| Claimed preparation | 2 | $15 \pm 1.2$ | $20 \pm 1.5$ | $315 \pm 14$ | $325 \pm 24$ |
| | 40 | $60 \pm 7.4^{**}$ | $17 \pm 4.1$ | $380 \pm 21^{*}$ | $243 \pm 10$ |
| Phenibut | 90 | $87 \pm 3.1^{}$ | $77 \pm 0.9^{}$ | $550 \pm 19^{}$ | $54 \pm 4^{}$ |

| Preparation 1 | Dose, mg/kg, animal weight 2 | Maximal effect appearance time from the start of experiment, in min. 7 | Nature of effect 8 |
|---|---|---|---|
| Control | | | |
| Claimed preparation | 2 | | |
| | 40 | 70 | episodic (1–2 episodes per hr) |
| Phenibut | 90 | 40 | Permanent (effective for over 3 hrs) |

*$p < 0.05$
**$p < 0.001$.

Thus, the experimental investigations in question have shown that the claimed preparation has antistressor and stress-protective effects and nootropic properties and, displaying at the same time a sedative and synchronizing effect on EEG, is devoid of the properties oftypicai tranquillizers and GABA derivatives, phenibut, which sharply inhibit motor activity as a dose is increased, as well as raise to a higher power the effect of hexenal, prolong hexenal sleep and simultaneously reduce the tonieo-extensor component of Corazol and strychnine twitches and electrical shock. The claimed preparation exhibits the highest efficiency in a dose of 1 to 2 mg/kg of weight and when increased, the degree of alterations explained by its effective dosage retains, which also is a fundamental distinction of the claimed preparation from benzdiazepines and GABA derivatives.

$LD_{50}$ of the claimed preparation have been detected on mice (a group of 50 animals weighing 25–30 g) and on rats (a group of 30 animals weighing 200–250 g). It has been established that with intragastric introduction, $LD_{50}$ is over 3000 mg/kg of animal weight and, hence, the claimed preparation is non-toxic.

The pathomorphological examination of animal's internal organs, after the repeated intragastric introduction of the of a table containing 184 pairs of prime numbers which are added up in pairs with account of the time of execution of the task. A test permits evaluating the rate of counting-computing operations per unit time (in. each and every minute), duration of execution of the task (time spent for adding 184 pairs of numbers), the number of mistakes, the speed of attention switching and the degree of weariness. The study of influence of a single dose of the claimed preparation on the speed of counting-computing operations shows that 30 min after the dose of the claimed preparation in 79.5% of cases of children and teenagers, the time for adding up numbers is reduced by 1.5–2 minutes and the number of errors diminishes twice in counting. No substantial changes took place in the control group of children in testing 30 minutes after a placebo was taken. The influence of the claimed preparation was investigated it produces on the speed of counting-computing operations with practically healthy adults and alcoholics. The results are given in Tables 10 and 11.

TABLE 10

Practically Healthy People

| Stages | Number of tested people | Speed of addition in pair/min, M ± m | Number of mistakes | Those making mistakes, % | Test reliability, p |
|---|---|---|---|---|---|
| Before taking a placebo | 20 | 48.0 ± 1.1 | 2 | 85 | — |
| 30 min after taking a placebo | 20 | 47.0 ± 1.7 | 1.9 | 80 | |
| Before taking the claimed preparation | 20 | 47.0 ± 1.8 | 2 | 80 | <0.05 |
| 30 min after taking the claimed preparation | 20 | 52.0 ± 1.9 | 1 | 40 | |

TABLE 11

Alcoholics

| Patient groups | Number of tested | Study stage | Addition pair/min, M ± m | Test reliability, p |
|---|---|---|---|---|
| Alcoholilc abstinence syndrome (2nd day) | 10 | Before taking the claimed preparation | 28.0 ± 1.0 | |
| | | After taking the claimed preparation | 32.0 ± 1.6 | <0.05 |
| Alcholyses (remission period) | 35 | Before taking the claimed preparation | 47.0 ± 1.2 | <0.05 |
| | | After taking the claimed preparation | 51.0 ± 1.8 | |

The claimed preparation was investigated for an effect it produces on attention, short-lived memory and sensomotor reactions of children of school age. The examination of attention was performed by using Schulte test which provides for a square chart produced before a patient (tested) that is divided into 49 squares containing confusedly arranged red and black numbers (24 and 25, respectively). The numbers are sought in the chart in strict order, say, red ones in increasing order and black ones in decreasing order, and along with this, the time is fixed for execution of the entire assignment, the time of search of each and every figure and the number of mistakes. The test makes it possible to assess attention and reveal the persons having enhanced emotional responses.

To study the state of short-lived memory, use was made of a test based on reproduction of two-digit numbers shown on the screen for 20 sec. With a repeated testing, there was exhibited a new series of numbers. Sensomotor reactions were evaluated with the aid of a visual-motor reaction (differentiation of optical signals from 20 applications).

Control and test groups carded out the entire volume of tests twice: the first investigation was assessed as initial (background), whereupon the test group of children received the claimed preparation one time in a dose of 2 mg/kg of weight; while the control one- a placebo, and the testing was repeated.

Investigations show that all pupils fulfilled a first series of tests (background) in full scope; nevertheless,, the majority of them observed fatigue: pronounced—10.4%, mild—18.7%, insignificant—62.5%, whilst 87.5% of the tested noted that the greatest of difficulties they encountered in remembering two-digit numbers due to high agitation and the lack of ability to focus, as well as in seeking numbers in Schulte test, the latter causing the pronounced nerve-psychic commotion of the persons under test that was accompanied by reddened faces, tremor of hands, and pronounced perspiration. The repeated testing in the test group has revealed a positive effect the claimed preparation has on emotional state, mental capacity, memory and attention. After taking the claimed preparation there was noticed (in 87.2% cases) the subjective and objective improvement of general state: disappearance of weariness, appearance of greater attentiveness and a calmer state in performing the tests. The results of the second testing are given in Table. 12.

The data of the table show that the volume of short-lived memory has increased on the average of 25% in 58.9% of cases and it did not worsen with 25.7% of the tested and remained on the initial level. With 56.4% of students, the claimed preparation caused a reduction of the latent period of a visual-motor reaction and the number of differentiation disruptions. The dose of the claimed preparation has markedly influenced attention as well, by reducing the attention switching time and the number of mistakes made.

With the children receiving a placebo there was observed, in 65% of cases of repeated examination, increased fatigue and decreased workability (worsening of memory by 20% and optical-motor reaction indices, and an increased attention switching time).

TABLE 12

| Mental capacity indices Stages of examination | Visual-motor reaction | | |
|---|---|---|---|
| | latent period in min. M ± m | differentiation disruption, in nominal units, M ± m | |
| 1 | 2 | 3 | |
| No dose of the claimed preparation | 0.53 ± 0.01 | 0.71 ± 0.15 | |
| After taking the preparation | 0.51 ± 0.01 | 0.46 ± 0.13 | |
| Test reliability, p | <0.05 | <0.05 | |
| 1 | 4 | 5 | 6 |
| No dose of the claimed prepar. | 38.97 ± 2.59 | 124.97 ± 10.17 | 6.64 ± 1.2 |
| After taking the preparation | 46.92 ± 2.58 | 95.39 ± 6.11 | 3.20 ± 0.39 |
| Test reliability, p | <0.05 | <0.05 | <0.05 |

In addition to an evaluation given to the indices reflecting mental capricity, the students were checked, during testings and taking exams, for a pulse rate and arterial pressure, which largely reflects the degree of nerve psychic tension. The results are given in Table 13.

Said data show that the claimed preparation eliminates a change in a pulse rate and arterial pressure in tested persons which occur in the conditions of heightened nerve-psychic agitation. In case of the claimed preparation being taken 30 minutes before an exam 95% of the students noted disappearance of fear and internal discomfort. The observations of an examiner-teacher confirm the fact that the behavior of children in preparing to and taking an examination was calmer, the children found a correct answer quicker and their marks exceeded those of the school year by 0.5–1 point, chiefly in math (80% had good and excellent marks 4 and 5; 60% - in the control). There have been conducted electrocardiographic investigations of the action the claimed preparation produces with a single dose thereof on the characteristics of cardiac rhythm of the pupils. The results are present in Table 14, wherefrom it is seen that the claimed preparation has a favorable effect of a human under test in case a nerve-psychic tension.

A study was made of influence of the claimed preparation, when taken chronically, on the mental workability of elementary form pupils who encounter difficulties in learning and who attend remedial classes. The control of the effective action of the claimed preparation was exercised with the use of corrective tests. Examination of the mental capacity dynamics of the tested was performed in two stages. During a first working week, an initial level of workability was determined daily; during a second week, the same workability indices were studied with the same children in experimental conditions against a background of the claimed preparation being taken. The results are presented in Table 15, from which we can see that the pupils demonstrated a relatively significant reduction of the index of the number of mistakes, against a background of the dose of the claimed preparation, by 500 signs before and after classes and an increased percentage of assignments fulfilled without mistakes. These results corroborate a positive influence the claimed preparation produces on attention and CNS functional state stimulation.

A study was also made of the claimed preparation when taken once or regularly (during 14 days), on the psycho-emotional state and the EEG indicators of teenagers with the deviation forms of behavior. Clinical and psychological investigations have shown that on taking the claimed preparation, weariness, irritation and internal unrest significantly abate.

TABLE 13

Influence of claimed preparation on heart beat dynamics/arterial pressure indicators of schoolboys with mental loading in heightened nerve-psychic tension conditions

| | Investigative stages | | |
|---|---|---|---|
| | Pulse frequency, spec./min., M ± m | Arterial pressure, mm Hg, M ± m | |
| | | systolic | diastolic |
| Lab conditions: | | | |
| I  background (before taking claimed preparation): | | | |
| a) prior to tests | 79.5 ± 1.8 | 110.1 ± 1.9 | 63.6 ± 1.5 |
| b) after testing | 89.8 ± 2.1 | 115.6 ± 2.8 | 71.5 ± 1.8 |
| test confidence, p | <0.05 | — | <0.05 |
| II  major (after taking claimed preparation): | | | |
| a) prior to tests | 76.8 ± 1.4 | 110.2 ± 1.7 | 69.3 ± 1.3 |
| b) after testing | 78.1 ± 1.4 | 107.7 ± 1.5 | 69.2 ± 1.1 |
| Investigations during exams: | | | |
| I  before the exams (without taking claimed preparation) | 95.7 ± 2.1 | 137.7 ± 3.1 | 70.0 ± 2.0 |
| II  after the exams: | | | |
| a) after taking claimed preparation | 72.8 ± 2.3 | 112.8 ± 2.8 | 65.7 ± 1.5 |
| b) without taking claimed preparation | 94.0 ± 2.4 | 140.1 ± 1.7 | 75.4 ± 1.8 |
| Test confidence, p | <0.05 | <0.05 | <0.05 |

TABLE 14

Influence of claimed preparation on schoolboy's heart-beat characteristic with mental loading in conditions of increased nerve-psychic tension

| | Investigative stages Heart-beat characteristics according to R. Baevsky Prognostication on the threshold of norm and pathology, 1979, Moscow, Meditsina Publishers, pp. 107–116) | | |
|---|---|---|---|
| | Mo. sec. M ± m | Amo. %, M ± m | Δx, sec. M ± m |
| 1 | 2 | 3 | 4 |
| 1. Background (before taking claimed preparation): | | | |
| a) prior to tests | 0.77 ± 0.02 | 33.4 ± 2.1 | 0.37 ± 0.01 |
| b) after performing tests | 0.75 ± 0.03 | 42.0 ± 1.8 | 0.28 ± 0.01 |
| Test confidence, p | — | <0.05 | <0.05 |
| II. Major investigations (after a dose of claimed preparation): | | | |
| a) prior to tests | 0.75 ± 0.03 | 32.0 ± 2.0 | 0.39 ± 0.01 |
| b) after testing | 0.74 ± 0.03 | 36.4 ± 2.2 | 0.38 ± 0.01 |

| | Investigative stages Heart-beat characteristics according to R. Baevsky Prognostication on the threshold of norm and pathology, 1979, Moscow, Meditsina Publishers, pp. 107–116) | |
|---|---|---|
| | Amo./Δx, M ± m | tension index, M ± m |
| 1 | 5 | 6 |
| 1. Background (before taking claimed preparation): | | |
| a) prior to tests | 94.1 ± 3.6 | 62.1 ± 4.1 |

TABLE 14-continued

Influence of claimed preparation on schoolboy's heart-beat characteristic with mental loading in conditions of increased nerve-psychic tension

|  |  |  |
|---|---|---|
| b) after performing tests | 154.6 ± 5.1 | 105.3 ± 3.5 |
| Test confidence, p | <0.05 | <0.05 |
| II. Major investigations (after a dose of claimed preparation): |  |  |
| a) prior to tests | 83.8 ± 4.0 | 57.6 ± 3.6 |
| b) after testing | 94.8 ± 14.1 | 65.3 ± 3.3 |

TABLE 15

Influence of claimed preparation on mental capacity of primary form schoolboys

| | Mental workability indicators Investigative stages week's second day | | | |
|---|---|---|---|---|
| | before classes without claimed | | after classes | |
| | prepar. dose | after dose | without- | after |
| Number of errors per 500 symbols M ± m | 11.4 ± 2.6 | 6.5 ± 1.6 | 12.1 ± 1.6 | 7.8 ± 1.8 |
| test confidence, p | <0.05 | | <0.05 | |
| Work without mistakes, % | 0 | 16.5 | 0 | 25.0 |

| | Mental workability indicators Investigative stages week's fourth day | | | |
|---|---|---|---|---|
| | before classes | | after classes | |
| | without dose | after dose | without dose | after dose |
| Number of errors per 500 symbols M ± m | 14.71 ± 2.4 | 7.6 ± 1.9 | 14.9 ± 2.4 | 8.4 ± 1.2 |
| Test confidence, p | <0.05 | | <0.05 | |
| Work without mistakes, % | 21.4 | 28.6 | 0 | 14.3 |

The EEG results are presented in Tables 16 and 17 from where one can see that the EEG of the tested subjects shows the positive dynamics of indicators both after one-time and regular doses of the claimed preparation. Moreover, on the basis of all the examined EEG indicators it has been established that the claimed preparation has nootropic activity and its action is directed to optimization of the CNS functional state and normalization of the speed of response of the brain. A placebo dose did not reveal the statistically important alterations of parameters of said electroencephalogram (Table 18) the data of which go to show that the "placebo effect" is accompanied, both after single and repeated doses, by the oppositely directed EEG indicators, which is not observed in the dynamics of EEG parameters on taking the claimed preparation.

So, the claimed preparation manifests pronounced anti-stressor and stress-protective effects and property to increase mental capacity (workability,) both in ordinary conditions and nerve psychic tension. Its application is most effective for increasing mental capacity in case of neuroses and neurosis-like states, the residual symptoms of cerebral trauma, deviation forms of behavior, alcoholism, and asthenia-vegetative disturbances. It is also effective as a stress-protector with the psycho-emotional agitation of practically healthy people.

The claimed preparation is absolutely safe, exhibits mild action and has no contraindications.

INDUSTRIAL APPLICABILITY

The claimed preparation of antistress, stressprotective and nootropic action finds application in adults' and children's practice in cases of attention/memory disturbances, reduced mental activity, neuroses, neUrosis-like states, cerebral residual symptoms, impediment of psychic development, deviation forms of behavior, alcoholism, and psychic-nerve agitation.

TABLE 16

| | Background EEG parameters Stages | | |
|---|---|---|---|
| | before a dose of claimed preparation | 1.5 hrs after a dose | after a two-week course dose |
| 1 | 2 | 3 | 4 |
| EEG variation, in arbitary units | a) 2.81 b) 1.81 | a) 2.89 b) 2.79* | 1) 3.00 b) 2.42* |
| Expression of ∝-rhythm in arbitary units, M ± m | 4.10 ± 0.23 | 4.89 ± 0.15** | 4.54 ± 0.31 |
| ∝d-index, % M ± m | 59.70 ± 5.00 | 74.60 ± 4.89** | 71.40 ± 6.40 |
| ∝-frequency, Hertz, M ± m | 10.20 ± 0.13 | 10.60 ± 0.11 | 10.40 ± 0.14 |
| ∝-oscillation amplitude mV, M ± m | 96.60 ± 4.80 | 105.70 ± 6.21 | 95.00 ± 5.16 |
| Expression of pathologically acute waves and peaked oscillation, arbitrary units, M ± m | 3.18 ± 0.11 | 1.71 ± 0.18** | 1.93 ± 0.16** |
| β-rhythm expression, arbitrary units, M ± m | 2.65 ± 0.08 | 2.14 ± 0.06** | 2.07 ± 0.11** |
| β-rhythm low-frequency expression, arbitrary units, M ± m | 1.81 ± 0.36 | 1.21 ± 0.31 | 1.29 ± 0.25 |
| β-rhythm amplitude, mV, M ± m | 28.10 ± 3.22 | 13.60 ± 2.01** | 16.40 ± 3.56 |
| Expression of bio-potential slow forms, arbitrary units, M ± m | 4.69 ± 0.24 | 2.85 ± 0.22** | 3.60 ± 0.26 |
| Slow wave index, %, M ± m | 42.20 ± 2.13 | 27.20 ± 2.61** | 31.70 ± 1.82** |
| Biopotential slow form amplitude, mV, M ± m | 75.00 ± 6.11 | 41.40 ± 5.51** | 44.20 ± 5.74 |
| Paroxysmal bursts, arbitrary units, M ± m | 3.30 ± 0.18 | 2.21 ± 0.15** | 3.00 ± 0.21 |

Note:
*difference with initial data (before a dose of the claimed preparation) according to Wilcoxon non-parametric criterion is actual, $p < 0.05$.
**difference with initial data (before a dose of the claimed preparation) is actual, $p < 0.05$.

TABLE 17

| | Reactive EEG parameters Stages | | |
|---|---|---|---|
| 1 | before a dose of claimed preparation 2 | 1.5 hrs after a dose 3 | after a two week course dose 4 |
| Eye opening-closing reaction: | | | |
| a) response, arbitrary units, M ± m | 3.27 ± 0.18 | 3.71 ± 0.27 | 3.07 ± 0.21 |
| b) biopotential amplitude decline, mV, M/m | 32.30 ± 4.11 | 25.40 ± 3.23 | 23.60 ± 4.16 |
| Attention mobilization: | | | |
| a) reaction expression, arbitrary units, M ± m | 1.97 ± 0.16 | 2.82 ± 0.08* | 3.21 ± 0.07* |
| Sonic signal count: | | | |
| a) reaction expression, arbitrary units, M ± m | 2.73 ± 0.17 | 3.64 ± 0.30 | 3.79 ± 0.15* |
| b) reaction suppression, sonic signals, M ± m | 10.50 ± 1.30 | 5.79 ± 0.94* | 6.57 ± 1.21 |
| Hv-reaction (test with hyperventilation): | | | |
| a) expression arbitrary units, M ± m | 3.58 ± 0.12 | 2.07 ± 0.07* | 2.64 ± 0.12 |
| b) after-effect, sec, M ± m | 33.20 ± 3.84 | 12.40 ± 2.51* | 20.70 ± 4.89 |
| Repeated response to eye opening-closing: | | | |
| a) reaction expression, arbitrary units, M ± m | 2.67 ± 0.26 | 3.73 ± 0.28 | 3.00 ± 0.23 |
| Presence of errors in count, %, M ± m | 63.00 ± 5.16 | 28.60 ± 4.68* | 33.00 ± 8.03* |

Note:
*difference with initial data (before taking the claimed preparation) is actual, $p < 0.05$.

TABLE 18

Background (reactive EEG of a control group of teenagers with deviation forms of behavior with placebo single) regular dose

| | EEG parameters Investigative Stages | | |
|---|---|---|---|
| 1 | before a placebo dose 2 | 1.5 hrs after a dose 3 | after a two week placebo course 4 |
| ∝-EEG variations, arbitrary units | a) 2.75 b) 1.76 | a) 2.69 b) 1.71 | a) 2.78 b) 1.79 |
| ∝-index, %, M ± m | 64.50 ± 4.05 | 70.80 ± 3.26 | 60.40 ± 3.18 |
| ∝-rhythm amplitude, mV, M ± m | 89.10 ± 4.32 | 86.30 ± 2.17 | 96.40 ± 4.96 |
| Expression of pathologic acute waves and peaked oscillation in arbitrary units, M ± m | 3.29 ± 0.20 | 2.84 ± 0.18 | 2.67 ± 0.17 |
| β-rhythm: | | | |
| a) expression arbitrary units, M ± m | 2.87 ± 0.13 | 2.68 ± 0.11 | 2.56 ± 0.15 |
| b) amplitude, mV, M ± m | 32.70 ± 2.85 | 26.90 ± 3.17 | 24.60 ± 3.24 |
| Response to eye opening-closing: | | | |
| a) reaction expression, arbitrary units, M ± m | 3.11 ± 0.13 | 2.82 ± 0.16 | 3.22 ± 0.16 |
| b) biopotential amplitude decline, mV, M ± m | 39.40 ± 2.19 | 38.20 ± 1.81 | 43.40 ± 2.42 |
| Attention mobilization: | | | |
| a) reaction expression arbitrary units, M ± m | 2.10 ± 0.09 | 1.89 ± 0.17 | 2.17 ± 0.11 |

We claim:

1. A method of enhancing mental capacity in a human wherein the mental capacity to be enhanced is memory, work ability, attention span or ability to calculate figures, comprising administering sublingually a composition in tablet form comprising from 0.1 to 0.2 g of glycine or a pharmaceutically acceptable salt thereof and methylcellulose.

2. A method according to claim 1 wherein the amount of methylcellulose present in the composition is from 0.5 to 2 weight %.

3. A method of enhancing mental capacity in a mammal wherein the mental capacity to be enhanced is memory and learning comprising administering sublingually a composition comprising from 0.1 to 0.2 g of glycine or a pharmaceutically acceptable salt thereof and methylcellulose.

4. The method according to claim 3 wherein the amount of methylcellulose present in the composition is from 0.5 to 2 weight %.

* * * * *